United States Patent [19]
Mohiuddin

[11] Patent Number: 5,322,512
[45] Date of Patent: Jun. 21, 1994

[54] SPLITTABLE NEEDLE FOR EPIDURAL ANESTHESIA

[75] Inventor: Mahmood Mohiuddin, Franklin, Mass.

[73] Assignee: The Kendall Company, Mansfield, Mass.

[21] Appl. No.: 76,921

[22] Filed: May 7, 1993

[51] Int. Cl.$^5$ ............................................. A61M 5/178
[52] U.S. Cl. .................................... 604/160; 604/177
[58] Field of Search ............... 604/158, 160, 161, 162, 604/171, 177

[56] References Cited

U.S. PATENT DOCUMENTS

| | | | |
|---|---|---|---|
| 3,598,118 | 8/1971 | Warren | 604/160 |
| 4,292,970 | 10/1981 | Hession | 604/158 |
| 4,377,165 | 3/1983 | Luther et al. | 604/160 |
| 4,512,351 | 4/1985 | Pohndorf | 607/117 |
| 5,141,497 | 8/1992 | Erskine | 604/160 |

FOREIGN PATENT DOCUMENTS

| | | | |
|---|---|---|---|
| 2929886 | 1/1981 | Fed. Rep. of Germany | 604/177 |
| 1437622 | 6/1976 | United Kingdom | 604/160 |

OTHER PUBLICATIONS

Travenol Auto Syringe Catalog No. LASML 01-001, 1985.

Primary Examiner—John G. Weiss
Attorney, Agent, or Firm—Alvin Isaacs

[57] ABSTRACT

Disclosed is a splittable needle device adapted for use in administering epidural anesthesia. The needle has guide means to facilitate insertion of the needle into the peridural space, contained on a splittable hub assembly.

8 Claims, 2 Drawing Sheets

SPLITTABLE NEEDLE FOR EPIDURAL ANESTHESIA

Prior surgical procedures for administering epidural anesthesia utilize an epidural catheter having a free proximal end. Following introducing the catheter within the needle and then into the body, the needle is withdrawn from the body and slid over the free proximal end of the catheter. The proximal end of the catheter is then secured to a catheter connector or adapter for placement in fluid communication with a source of the liquid anesthesia for administering to the patient.

To guard against overtightening of the catheter connector, causing damage to the catheter and/or its function, or undertightening or accidental loosening whereby the catheter slips out of the connector, as well as the problem which sometimes occurs of accidentally dropping the connector while attempting to secure it to the catheter, it would be desirable to employ an epidural catheter pre-connected at its proximal end to an adapter.

However, if this is done, it will be appreciated that it would no longer be possible to slide the needle over the proximal end of the catheter which has been introduced through the needle into the body.

A particularly efficacious way of solving this dilemma is to employ a so-called splittable needle, which needle is per se old in the art for other medical procedures and is disclosed, for example, in U.S. Pat. Nos. 4,377,165 of Luther et al and 4,449,973 of Luther, both assigned to Luther Medical Products, Inc.

Stated simply, the task of this invention is to design a splittable needle device which has guide means facilitating the delicate task of inserting the needle within the peridural space without penetrating the arachnoid membrane, which needle assembly is readily splittable away from the catheter therewithin.

BRIEF DESCRIPTION OF THE INVENTION

In accordance with this invention, the task is solved in an elegant manner by providing a splittable needle having a splittable hub assembly including a guide member which can be gripped by the anesthesiologist to gently guide the needle into the desired position, the needle and the hub assembly thereafter being readily separable from the catheter in a single manipulative step.

DETAILED DESCRIPTION OF THE INVENTION

As previously mentioned, the present invention is directed to a so-called split or break-away needle for use in administering epidural anesthesia, the needle being characterized by having means facilitating insertion of the needle into the peridural space.

The invention will best be understood by reference to the accompanying illustrative drawings taken in conjunction with the following detailed description.

Figure 1:
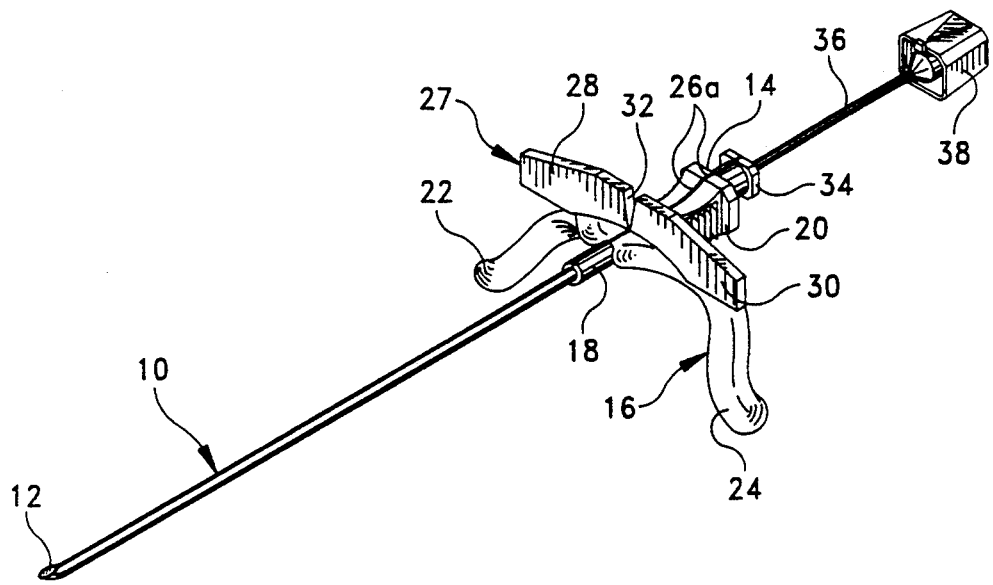
FIG. 1 is a perspective view of a novel split needle device of this invention.
Figure 2:
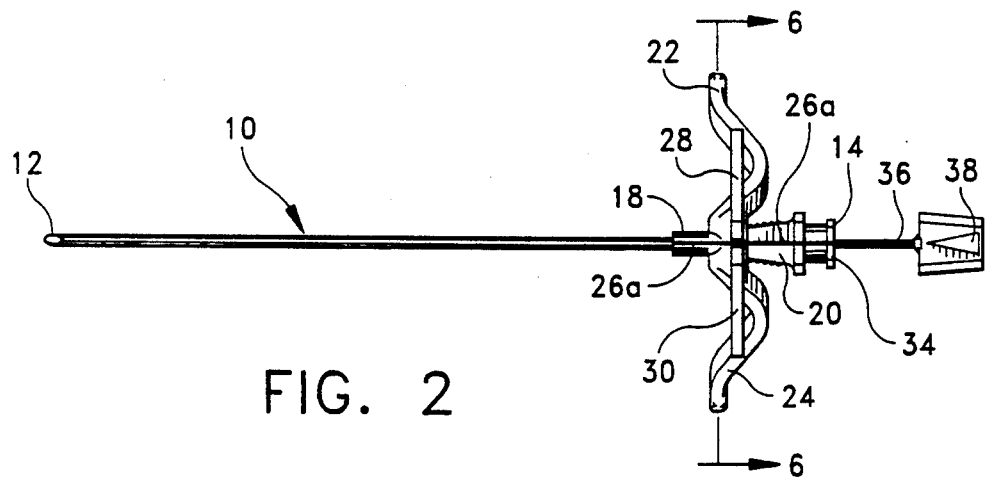
FIG. 2 is a top plan view of the device of FIG. 1.
Figure 3:
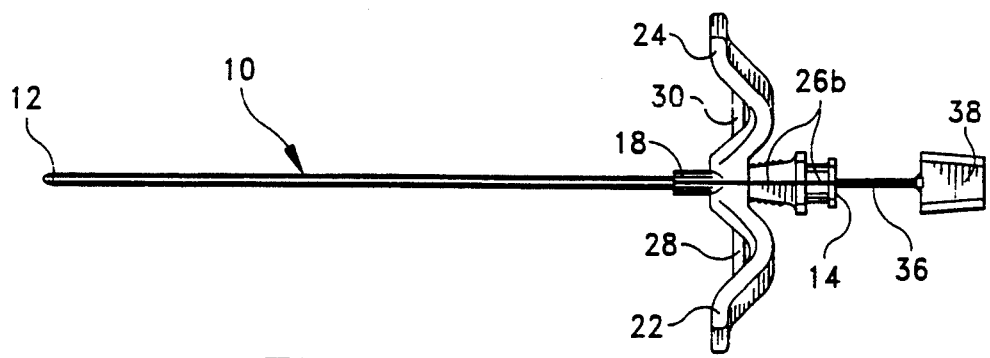
FIG. 3 is a bottom plan view of the device of FIG. 1.

As shown in the drawings, the needle 10 has a distal or leading end 12 and a proximal or trailing end 14 at which a unitary hub assembly 16 is provided. Intermediate the distal and proximal ends 18, 20, respectively of the hub assembly a pair of opposed wings 22, 24, are provided for splitting the needle away from the catheter, as will be described hereinafter. As best seen in FIGS. 2 and 3, the hub assembly 16 has a pair of slits 26a, 26b extending between the distal and trailing end 18, 20 of the assembly, the slits being essentially parallel and being situated radially approximately 180° apart.

A guide bar 27 is provided above wings 22, 24 to facilitate inserting the needle without touching wings 22 and/or 24 which could cause inadvertent premature splitting of the needle 10 and separation from the catheter within the needle.

In a preferred form, the guide bar 27 comprises substantially equal sections 28, 30 separated at least at their upper surface by slit 32. As shown in the drawings, slit 32 extends substantially through guide bar 27 to the base or bottom members of guide bar sections 28, 30 which in the unitary hub assembly will be adhered to wings 22, 24, respectively.

The proximal end 20 of the hub assembly 16 will be provided with a conventional luer fitting 34 for receiving a syringe.

While not an essential component of the invention, to facilitate insertion of the needle, a stylet 36 having a cap 38 of per se known structure and configuration is preferably employed. The stylet will be of a length such that when inserted into the needle, the leading end (not shown) of the stylet will extend to the distal tip of the needle while the cap 38 abuts the rear of luer fitting 34.

The splittable needle employed in the practice of this invention may be of the type described and claimed in the aforementioned U.S. Pat. No. 4,377,165 of the Luther et al.

As is described therein, a needle blank is continuously formed from flat sheet metal such as sections or from a roll. A groove of controlled depth is formed along the blank stock which is then rolled to a hollow configuration and then cut into individual needle barrels with a longitudinal slit along each needle barrel. The groove is oriented parallel to the slit and along the opposite side of the barrel. Finally, the wings are welded to the barrel on each side of the slit. The groove depth is sufficiently shallow to ensure adequate stiffness during use while being deep enough so that the needle will split easily when the wings are flexed, thereby separating the needle from the catheter.

As further described in the patent, excellent stiffness, splitting and rolling properties are obtained with a sheet thickness of about 2–4 mils, a needle length of about ¾"–2", about 12–20 gauge barrel diameter, and a controlled groove depth about 50%±10% of the sheet thickness using a 304–316 stainless steel or equivalent.

The sheet stock may be in flat form such as in sections, say, ½-10 feet long, but is usually loaded on a roll. The open needle portion constitutes only about 7%-15% of the total barrel length, and this considerably improves the working strength of the needle. Thus, the needle of this invention can employ a relatively deep groove without losing structural integrity during use.

While the needles contemplated by this invention may be made in the same manner, it is pointed out that epidural needles are longer than the ¾ inch to 2 inches recited in the patent. Specifically, the epidural needles of this invention will typically be about 3.5 inches in length.

Figure 4:
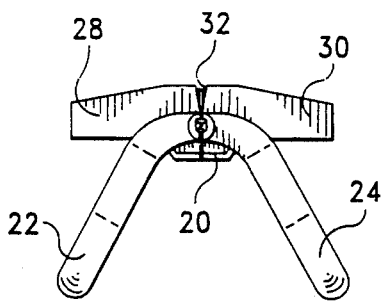
FIG. 4 is a front elevational view taken from the leading (distal) end of the device of FIG. 1.
Figure 5:
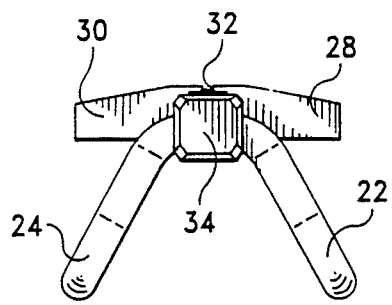
FIG. 5 is a rear elevational view taken from the trailing (proximal) end.
Figure 6:
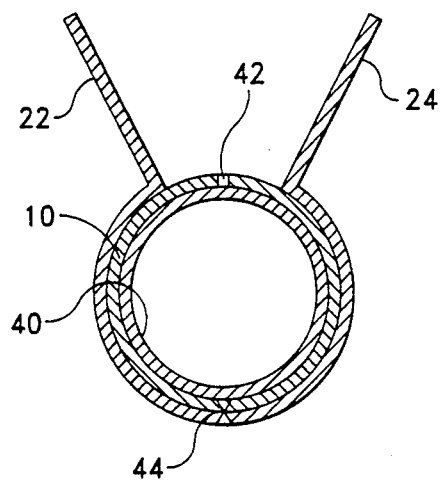
FIG. 6 is an enlarged cross section view of the needle taken along lines 6—6 of FIG. 2.
Figure 7:
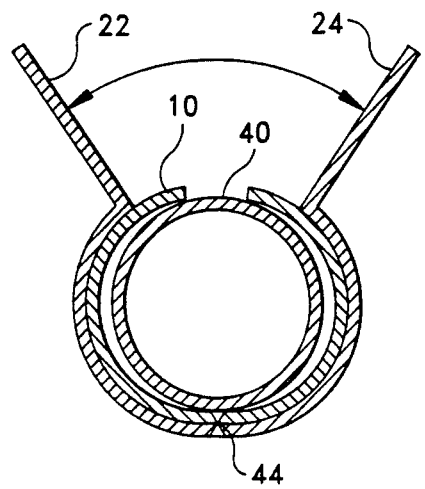
FIG. 7 is a cross section view of the needle similar to FIG. 6 showing the effects of flexing the wings to split the needle and thereby separate the needle from the catheter within the needle.

The structure of the needle barrel and how splitting is effected may best be understood by reference to FIGS. 6 and 7 of the application which correspond essentially to FIGS. 3 and 4 respectively of U.S. Pat. No. 4,377,165.

As shown therein, the needle has a longitudinal slit 42 extending the entire length of the needle barrel between its ends 12, 14. The slit is formed when the blank is rolled to produce the barrel and may typically, for example be as great as 1 mil wide.

Groove 44 is formed on the inner wall 10a of the needle barrel also extending longitudinally from one end to the other. As shown, groove 44 is situated about 180° radially from slit 42 and is parallel thereto.

The procedure for introducing the needle into the peridural space for administering epidural anesthesia will now be described.

To administer epidural anesthesia, great care must be taken in inserting the needle to be sure it is positioned in the peridural space between the ligamentum flavum and the arachnoid membrane. As is well understood, if the needle penetrates too far, it will penetrate into the subarachnoid space, causing spinal fluid to leak out. For this reason, the needle may be calibrated to assist the anesthesiologist in determining the degree of insertion into the body.

In a typical procedure, the patient, having been prepped for surgery, is brought into an induction room adjacent the operating room where the anesthesiologist is to insert the catheter in preparation for the surgery.

A local injection is first given to minimize pain and discomfort from introducing the needle. With the stylet in the needle, the needle is slowly and carefully inserted until it abuts the ligamentum flavum, at which time the skilled hands of the anesthesiologist senses a resistance to further insertion. At this time, the stylet is removed from within the needle and a "loss of resistance" syringe is inserted within the luer fitting. By slowly advancing the needle and syringe, the ligamentum flavum is penetrated and the needle tip is advanced into a vacuum area (the peridural space) where there is no resistance.

At this point, the syringe is withdrawn and the catheter inserted within the needle and then into the peridural space.

With the conventional needle procedures, the catheter is secured in place, as with adhesive tape, and the needle is withdrawn over the catheter. When the needle is removed, the proximal end of the catheter may be secured within the distal end of a catheter adapter or connector having a luer fitting at its proximal end to put a syringe filled with liquid anesthesia in fluid communication with the catheter secured to the distal end of the connector. As an example of such an adapter, mention may be made of the adapter described and claimed in U.S. Pat. No. 5,053,015 assigned of Gross, to The Kendall Company, assignee of the present invention and commercially available under the trademark Safe Trak.

As distinguished from this conventional system, the present invention contemplates the use of an epidural catheter which is preconnected to the adapter at its proximal end, thereby obviating the need to perform the connection in the surgical procedure along with the inherent dangers of dropping the connector so that a new one is required, overtightening the connection to impair the catheter function and/or undertightening so that the catheter accidentally is removed or drops from the connector.

While a preconnected epidural catheter accordingly has obvious inherent advantages, it will of course be appreciated that in view of the preconnection, it is not possible to slide the needle over the proximal (trailing) end of such a catheter.

This problem is then solved by employing the splittable needle to which this invention is directed.

While splittable needles are per se known for other medical procedures, it was never heretofore been suggested for use in epidural anesthesia to the best of Applicant's knowledge.

With reference against to FIGS. 6 and 7, in the prior medical procedures, the needle will be gripped along its barrel or gently by the wings and inserted beneath the skin to the desired placement. After placement, the wings 22, 24 may be flexed in the direction shown by the arrows in FIG. 7, causing the needle to open up along the longitudinal slit 42, thereby causing splitting or cracking along the longitudinal groove 44 which in turn causes the needle halves following splitting to separate from the catheter 40 within the needle.

For use for epidural anesthesia has contemplated by this invention, it is essential that the split needle device have guide means, e.g. the illustrated guide bar 27 for gripping or pushing against (as desired by the anesthesiologist) during the delicate procedure of slowly and carefully introducing the needle into the peridural space.

As seen, the split needle device of this invention also utilizes a one-piece splittable hub assembly 16 wherein the wings, guide bar and other components of the assembly all split away from the catheter along with the needle upon flexing the wings 22, 24, the splitting of the hub assembly being assured by slits 26a and 26b.

From the foregoing description it will be appreciated that the present invention provides an elegant design for a splittable needle for use in epidural anesthesia.

The guide bar 27 is versatile and ergonomic in design in that it caters to the particular style or whim of the user in gripping to guide the needle into the peridural space. Whatever the user's preference, a secure grip is provided.

The longitudinal slits 26a,b ensure splitting of the hub assembly along with the needle barrel for a clean separation of the catheter.

It will be appreciated that various changes may be made without departing from the scope of the invention herein contemplated.

For example, other splittable needle constructions may be readily suggested to those skilled in the art in the light of the foregoing description as will other designs for the guide means and/or the wing configuration for causing splitting of the needle.

Accordingly, all matter contained in the foregoing descriptions and shown in the accompanying drawings shall be interpreted as being illustrative and not in a limiting sense.

What is claimed is:

1. A splittable needle device through which a catheter may be introduced into the peridural space of a patient for administering epidural anesthesia from a source of the anesthesia, comprising;
    (a) an epidural needle having a barrel portion with inner and outer walls and opposed distal and proximal ends, the needle being splittable from its distal to its proximal end, whereby to be separable from the catheter inserted therewithin upon splitting;
    (b) a hub assembly secured around the proximal end of the needle;
    (c) means for splitting the needle and the hub assembly to separate the device from the catheter, the splitting means including flexing wings secured to the needle and to the hub assembly so as to cause splitting of each of the needle and the hub assembly upon flexing of the wings; and
    (d) guide means separate from the splitting means for gripping to facilitate insertion of the needle without touching the splitting means which can cause inadvertent premature splitting of the needle, the guide means consisting essentially of a guide bar seated on and secured to the flexing wings, the guide bar having two substantially equal longitudinal sections, each having upper and lower longitudinal surfaces, the two sections being separated at their upper surface by a slit, the slit extending substantially through the guide bar to the lower surface of the guide bar.

2. A splittable needle device as defined in claim 1 wherein the hub assembly as distal and proximal ends and a pair of slits extending between the distal and trailing ends of the hub assembly, the slits being essentially parallel and being situated radially approximately 180° apart to facilitate splitting of the hub assembly from its distal to its proximal end upon flexing the wings secured to the hub assembly.

3. A splittable needle device as defined in claim 2 wherein the needle has a longitudinal slit extending the entire length of the needle barrel between the ends of the needle, the needle having a groove on the inner wall of the barrel also extending longitudinally between the ends of the needle, the groove being situated approximately 180° radially from the slit in the needle barrel and being parallel thereto, the groove depth being sufficiently shallow to ensure adequate stiffness during use while being deep enough so that the needle will split easily when the wings are flexed, thereby concurrently separating both the hub assembly and the needle from the catheter within the splittable needle.

4. A splittable needle device as defined in claim 3 wherein the proximal end of the hub assembly has a luer fitting for receiving the leading end of a syringe.

5. A splittable needle device through which a catheter may be introduced into the peridural space of a patient for administering epidural anesthesia from a source of the anesthesia comprising;
    (a) an epidural needle splittable longitudinally and having opposed distal and proximal ends and a barrel portion with inner and outer walls extending between the opposed ends of the needle;
    (b) a hub assembly secured around the proximal end of the needle, the hub assembly having a pair of slits extending between the ends of the hub assembly, the slits being essentially parallel and being situated radially approximately 180° apart;
    (c) flexing wings secured to the needle and to the hub assembly so as to cause splitting needle and the hub assembly upon flexing of the wings so that the needle device can be separated from a catheter inserted therein for administering the epidural anesthesia; and
    (d) a guide bar for gripping to facilitate insertion of the needle without contacting the flexing wings, which contacting can cause inadvertent premature splitting of the needle, the guide bar being seated on and secured to the flexing wings, the guide bar having two substantially equal longitudinal sections, each having upper and lower longitudinal surfaces, the two sections being separated at their upper surface by a slit, the slit extending substantially through the guide bar to the lower surface of the guide bar.

6. A splittable needle device as defined in claim 5 wherein the needle has a longitudinal slit extending the entire length of the needle barrel between the ends of the needle, the needle having a groove on the inner wall of the barrel also extending longitudinally between the ends of the needle, the groove being situated approximately 180° radially from the slit in the needle barrel and being parallel thereto, the groove depth being sufficiently shallow to ensure adequate stiffness during use while being deep enough so that the needle will split easily when the wings are flexed, thereby concurrently separating both the hub assembly and the needle from the catheter within the splittable needle.

7. A splittable needle device as defined in claim 6 wherein the proximal end of the hub assembly has a luer fitting for receiving the leading end of a syringe.

8. A method for administering epidural anesthesia comprising the steps of:
    (a) inserting a needle as defined in claim 5 into the peridural space of a patient;
    (b) introducing an epidural catheter through the needle and into the peridural space;
    (c) thereafter flexing the wings to split the needle device and thereby separate it from the catheter while retaining the catheter in place; and
    (d) thereafter introducing a liquid anesthesia into the peridural space through the proximal end of the catheter.

* * * * *